United States Patent
Chen et al.

(10) Patent No.: US 11,435,325 B2
(45) Date of Patent: Sep. 6, 2022

(54) METHOD FOR DETECTING SELENOAMINO ACID IN SELENOPROTEIN

(71) Applicant: Enshi Tujia and Miao Autonomous Prefecture Academy of Agricultural Sciences (Enshi Tujia . . ., Hubei (CN)

(72) Inventors: Yongbo Chen, Hubei (CN); Shuqin Liu, Hubei (CN); Chaoyang Zhang, Hubei (CN); Baishun Hu, Hubei (CN); Weidong Li, Hubei (CN); Guangyu Huang, Hubei (CN); E Chen, Hubei (CN); Bang Qin, Hubei (CN); Yong Qu, Hubei (CN)

(73) Assignee: ENSHI TUJIA AND MEAO AUTONOMOUS PREFECTURE ACADEMY OF AGRILCULTURAL SCIENCE (ENSHI TUJIA AND MIAO AUTONOMOUS PREFECTURE SELENIUM APPLICATION TECHNOLOGY AND PRODUCT DEVELOPMENT INSTITUTE), Hubei (CN)

(*) Notice: Subject to any disclaimer, the term of this patent is extended or adjusted under 35 U.S.C. 154(b) by 252 days.

(21) Appl. No.: 16/998,081

(22) Filed: Aug. 20, 2020

(65) Prior Publication Data
US 2021/0148867 A1 May 20, 2021

(30) Foreign Application Priority Data
Nov. 19, 2019 (CN) .......................... 201911133352.3

(51) Int. Cl.
| G01N 30/06 | (2006.01) |
| G01N 30/74 | (2006.01) |
| G01N 33/68 | (2006.01) |
| G01N 30/96 | (2006.01) |
| G01N 1/44 | (2006.01) |
| G01N 30/02 | (2006.01) |

(52) U.S. Cl.
CPC ............. *G01N 30/06* (2013.01); *G01N 30/74* (2013.01); *G01N 33/68* (2013.01); *G01N 2030/027* (2013.01)

(58) Field of Classification Search
CPC .... G01N 30/74; G01N 33/6812; G01N 33/68; G01N 30/06; G01N 1/44; G01N 30/96
USPC ................................................... 436/90, 172
See application file for complete search history.

(56) References Cited

U.S. PATENT DOCUMENTS

| 5,015,445 A * | 5/1991 | Doleman ................. G01N 1/44 422/562 |
| 2017/0023572 A1* | 1/2017 | Naser ..................... C12Q 1/689 |

OTHER PUBLICATIONS

Chen, S.-T. et al, International Journal of Peptide and Protein Research 1987, 30, 572-576.*
Gomez-Ariza, J. L. et al, Analytica Chimica Acta 2004, 520, 229-235.*
Gomez-Ariza, J. L. et al, Analytica Chimica Acta 2004, 524, 305-314.*
Sanchez-Rodas, D. et al, Talanta 2013, 106, 298-304.*
Maher, W, et al, Microchemical Journal 2016, 126, 92-95.*

* cited by examiner

*Primary Examiner* — Arlen Soderquist
(74) *Attorney, Agent, or Firm* — Tutunjian & Bitetto, P.C.

(57) ABSTRACT

The present invention belongs to the technical field of analysis and detection and provides a method for detecting a selenoamino acid in a selenoprotein. The detection method includes: (1): mixing 10-30 mg of a selenoprotein sample with hydrochloric acid, and hydrolyzing with microwaves at 140-170° C. for 10-40 min to obtain a hydrolysate; (2): adjusting pH of the hydrolysate to 6-8 to obtain a pretreated solution; and, (3): detecting a selenoamino acid in the pretreated solution with high performance liquid chromatography-hydride generation-atomic fluorescence spectrometry (HPLC-HG-AFS) to obtain a content of the selenoamino acid. The method is simple in operation and provides an accurate and reliable result, and also reduces time and cost.

9 Claims, 3 Drawing Sheets

METHOD FOR DETECTING SELENOAMINO ACID IN SELENOPROTEIN

TECHNICAL FIELD

The present invention belongs to the technical field of analysis and detection, in particular relates to a method for detecting a selenoamino acid in a selenoprotein.

BACKGROUND

A selenoprotein, one of the major forms of biological organic selenium (Se), is widely present in raw materials of Se-rich products (for example, Se yeasts and selenoprotein powders), health products (for example, Se-rich protein tablets and capsules) and Se-rich products. A method for detecting a selenoamino acid in a selenoprotein has always been a research and development hot spot for researchers. Instrumental analysis methods can include high performance liquid chromatography inductively coupled plasma mass spectrometry (HPLC-ICP-MS), high performance liquid chromatography hydride generation atomic fluorescence spectrometry (HPLC-HG-AFS) and the like. However, a sample pretreatment method still relies on an enzymatic hydrolysis method imported from abroad. The enzymatic hydrolysis pretreatment method has complicated operations (multiple times of adding an enzyme and shaking) with a long time (more than 30 h), a high cost (an expensive reference substance with several thousand RMB for analysis of one sample) and incomplete hydrolysis (presence of both peptide chains and selenoamino acids, with a molecular weight of around 20,000 Daltons). Therefore, the enzymatic hydrolysis method is not suitable for a wide range of applications.

SUMMARY

In view of this, an objective of the present invention provides a method for detecting a selenoamino acid in a selenoprotein. The detection method implemented by hydrolyzing a selenoprotein with microwaves, and then detecting a selenoamino acid using HPLC-HG-AFS. The method is simple in operation and provides an accurate and reliable result, and reduces time and cost.

In order to realize the objective of the present invention, the present invention provides the following technical solutions.

The method for detecting a selenoamino acid in a selenoprotein,:

(1): mixing 10-30 mg of a selenoprotein sample with hydrochloric acid, and hydrolyzing with microwaves at 140-170° C. for 10-40 min to obtain a hydrolysate;

(2): adjusting a pH of the hydrolysate to 6-8 to obtain a pretreated solution;

(3): detecting a selenoamino acid in the pretreated solution using HPLC-HG-AFS to obtain a content of the selenoamino acid.

In one embodiment, the selenoprotein sample is 15-25 mg.

In another more preferred embodiment, the selenoprotein sample is 20 mg.

According to another preferred embodiment, the hydrolyzing with microwaves is carried out at 150-160° C.

In yet another preferred embodiment, the hydrolyzing with microwaves is carried out or performed for 30-40 min.

According to another preferred embodiment, the pretreated solution has a pH of 7-8.

In yet a further embodiment, the HPLC preferably uses an anion exchange column.

According to the invention, the content of the selenoamino acid can be detected within 8 min after a test sample is well prepared.

The present invention provides a method for detecting a selenoamino acid in a selenoprotein, including: (1): mixing 10-30 mg of a selenoprotein sample with hydrochloric acid, and hydrolyzing with microwaves at 140-170° C. for 10-40 min to obtain a hydrolysate; (2): adjusting pH of the hydrolysate to 6-8 to obtain a pretreated solution; and, (3): detecting a selenoamino acid in the pretreated solution with or using HPLC-HG-AFS to obtain a content of the selenoamino acid. The detection method is implemented by hydrolyzing a selenoprotein with microwaves, and then detecting a selenoamino acid by HPLC-HG-AFS. The selenoprotein is hydrolyzed with microwaves and decomposed into selenocystine ($SeCys_2$), selenomethionine (SeMet), selenomethyl-L-selenocysteine (SeMeCys) and other free Se-containing small molecular substances, namely selenoamino acids. The hydrolysate having an adjusted pH is passed through HPLC to separate the selenoamino acid which then enters the HG and is converted into hydrogen selenide ($H_2Se$) which is in turn brought to the AFS by a carrier gas (argon) for detection.

The method for detecting the present invention is simple in operation and reduces time and cost. Moreover, the present invention makes comprehensive considerations on interactions of various factors and determines relatively optimal conditions for hydrolyzing a selenoprotein with microwaves to obtain complete hydrolysis within a short time and with an accurate and reliable result. A sum of the Se contents of various forms of the selenoprotein (in terms of Se) measured by the method for detecting of the present invention is consistent with the total Se content measured by the method in the national standard GB 5009.93-2017. Therefore, the present invention can quickly and accurately detect the selenoamino acids in various selenoproteins and remains in compliance with the national standard.

DETAILED DESCRIPTION

Figure 1:
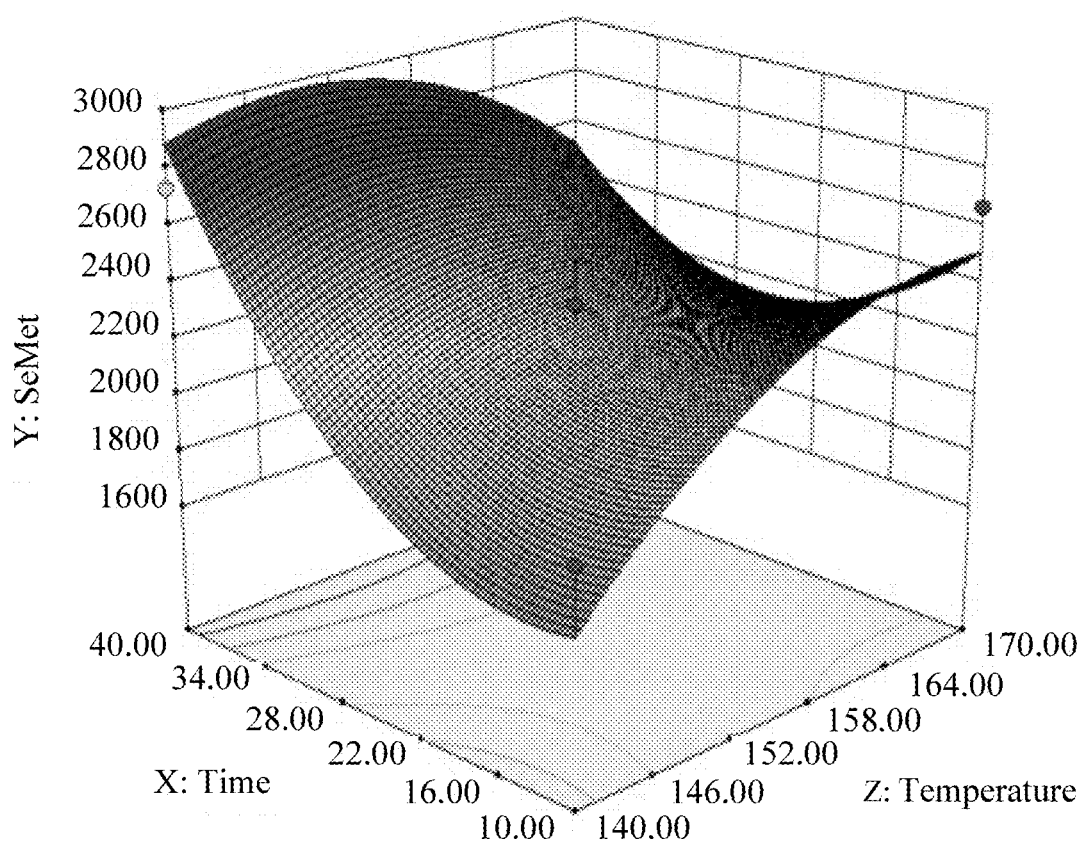
FIG. 1 is a graphical representation of the response surface of Y=f (A, B) in Example 2, where Y is the content of SeMet in the hydrolysate, A is the hydrolysis temperature, and B is the hydrolysis time.

The present invention provides a method for detecting a selenoamino acid in a selenoprotein, including the following:

(1): mixing 10-30 mg of a selenoprotein sample with hydrochloric acid, and hydrolyzing with microwaves at 140-170° C. for 10-40 min to obtain a hydrolysate;

(2): adjusting pH of the hydrolysate to 6-8 to obtain a pretreated solution;

(3): detecting a selenoamino acid in the pretreated solution with HPLC-HG-AFS to obtain a content of the selenoamino acid.

In the present invention, the selenoprotein sample is mixed with hydrochloric acid and hydrolyzed with microwave to obtain a hydrolysate. According to an embodiment, the selenoprotein sample can be in a range of 10-30 mg, and is preferably in a range of 15-25 mg, and even more preferably 20 mg. According to an embodiment of the invention, the hydrochloric acid preferably has a molar concentration of 6 mol/L; and a ratio of the hydrochloric acid to the selenoprotein sample is 1 mL: (10-30) mg. In one embodiment, the hydrolyzing is carried out at a temperature range of 140-170° C., and in a further embodiment, preferably 150-160° C., and in yet another embodiment, more preferably 150° C. for 10-40 min according to one embodiment, and in a further embodiment, preferably 30-40 min, and yet another embodiment, more preferably 40 min. The hydrolyzing with microwaves is preferably carried out in a microwave proteolysis apparatus. The present invention has no special requirements on the microwave proteolysis apparatus, and an apparatus well known in the art may be used. The present invention has no special requirements on parameters set for the microwave proteolysis apparatus as long as a temperature required for hydrolysis can be obtained. The present invention also has no special requirements on specific operations of the microwave proteolysis apparatus, and operations well known in the art may be used. According to the present invention, the selenoprotein is hydrolyzed with microwaves and decomposed into $SeCys_2$, SeMet, SeMeCys and other free Se-containing small molecular substances, namely selenoamino acids. Compared with the enzymatic hydrolysis pretreatment method, the method of the present invention is simple in operation and reduces the time and cost. Moreover, the conditions for hydrolyzing a selenoprotein with microwaves in accordance with the present invention are determined after comprehensive considerations on the interactions of various factors to ensure complete hydrolysis within a short time and an accurate and reliable result.

After the hydrolysate is obtained, the pH of the hydrolysate is adjusted to 6-8 to obtain a pretreated solution. In one preferred embodiment, the pH of the pretreated solution is 7-8, and another more preferred embodiment 7.5. The pH of the hydrolysate is preferably adjusted using sodium hydroxide.

After a pretreated solution is obtained, a selenoamino acid in the pretreated solution is detected using high performance liquid phase-hydride generation-atomic fluorescence spectrometry (HPLC-HG-AFS) to obtain a content of the selenoamino acid. According to one embodiment, the pretreated solution is preferably filtered with a 0.45μM syringe filter to obtain a filtrate before detection. The HPLC preferably uses an anion exchange column under conditions as shown in Table 1. The conditions for the HG (a pretreatment device for morphological analysis) are shown in Table 2 and conditions for the AFS are shown in Table 3. According to a preferred embodiment of the present invention, the pretreated solution is used for detecting with HPLC-HG-AFS where the content of the selenoamino acid can be detected preferably within 8 min after a test sample is well prepared.

TABLE 1

Conditions for HPLC (with an anion exchange column)

| Procedure | Name of parameter | Setting of parameter |
|---|---|---|
| HPLC | Column | XP anion exchange column (250 mm × 4.6 mm i.d., 5 μm) |
|  | Mobile phase | 40 mM $(NH_4)_2HPO_4$, pH adjusted to 6.0 with HCOOH |
|  | Flow rate | 1.0 mL/min |
|  | Elution | Isocratic elution |

TABLE 2

Conditions for HG

| Procedure | Name of parameter | Setting of parameter |
|---|---|---|
| HG | Oxidant | 0.5% (m/v) KOH + 2.0% (m/v) KI |
|  | Reducing agent | 0.5% (m/v) KOH + 1.5% (m/v) $KBH_4$ |
|  | Carrier flow | 10% (v/v) HCl |
|  | Ultraviolet (UV) lamp on/off | UV on |
|  | Pump speed | 65 r/min |

TABLE 3

Conditions for AFS

| Procedure | Name of parameter | Setting of parameter |
|---|---|---|
| AFS | Element lamp | Se |
|  | Negative high pressure | 300 V |
|  | Lamp current (total current/auxiliary current) | 80/40 mA |
|  | Carrier gas | 300 mL/min |
|  | Shielding gas | 600 mL/min |

In accordance with an embodiment of the invention, the hydrolysate having an adjusted pH is passed through high performance liquid chromatography (HPLC) to separate the selenoamino acid which enters the hydride generation (HG) and is converted into hydrogen selenide ($H_2Se$) which is in turn brought to the atomic fluorescence spectrometry (AFS) by a carrier gas (argon) for detection. According to the present invention, the detecting a selenoamino acid in the pretreated solution with HPLC-HG-AFS is carried out with qualitative analysis by retention time and quantitative analysis by an external standard method.

The method for detecting the present invention has simple operations which can quickly and accurately detect the selenoamino acids in various selenoproteins and suitable for use in a wide range of applications.

The method for detecting a selenoamino acid in a selenoprotein provided by the present invention is described in detail below with reference to some examples, but the examples shall not be understood or considered as limiting the protection scope of the present invention.

EXAMPLE 1

A selenoprotein hydrolysate obtained by hydrolysis with microwaves was a strong acid solution whose pH needed to be adjusted before detection on a machine. The selenoamino acids $SeCys_2$, SeMet and SeMeCys were neutral amino acids. Standard solutions were obtained by dissolving these amino acids in water and had a pH of about 5.8, while the mobile phase of HPLC had a pH of 6.0. Thus, the pH of the hydrolysate should be adjusted to an appropriate value. In this experiment, the pH of the hydrolysate was adjusted to 6.0-8.0 to observe effect of the pH of the hydrolysate on detection of selenoamino acids. The HPLC-HG-AFS method was used to detect the selenoamino acids in the hydrolysates with detection conditions shown in the above Table 1, Table 2 and Table 3, and results shown in Table 4 below (the main product of selenoprotein hydrolysis was SeMet, so this example focused on effect on detection of SeMet).

TABLE 4

Effect of pH of selenoprotein hydrolysate on detection of selenoamino acid

| pH of hydrolysate | 6.0 | 6.5 | 7.0 | 7.5 | 8.0 |
|---|---|---|---|---|---|
| Content of SeMet (mg/kg) | 1687.98 | 1810.01 | 2121.53 | 2085.72 | 1867.16 |
| Content of total Se (mg/kg) | 1869.34 | 1989.55 | 2284.83 | 2486.89 | 2705.51 |

It can be seen from Table 4 that the pH of the hydrolysate had an effect on the response value of SeMet and the total Se content. With increase of the pH, the response value of the total Se content increased, and the content of the SeMet increased at first and then decreased. In view of the total Se content in the selenoprotein of 2408.55 mg/kg measured according to GB 5009.93-2017, detection results in this example were closest to the national standard measurement when the hydrolysate had a pH of 7.0 and 7.5. The predicted values for SeMet were also closest to the standard measurement when the SeMet had a pH of 7.0 and 7.5 (a model established by a response surface method predicting a value of 2195.16 mg/kg). To facilitate operation, the pH of the hydrolysate was adjusted to 7.5.

EXAMPLE 2

In this example, a central composite design-response surface method was used to verify the conditions for hydrolyzing with microwaves with steps as follows:

Step (1): Setting of experimental factors and levels.

Hydrolysis temperature with microwaves (140-170° C.), hydrolysis time (10-40 min) and sample weight (10-30 mg) were used as independent variables (the pH of the hydrolysate was adjusted to 7.5), and content of a selenoamino acid and total Se in the hydrolysate were used as dependent variables. Multiple linear regression and quadratic fitting were performed on various levels of the independent variables, and the optimal hydrolysis conditions were selected using a response surface method. The experimental factors and corresponding levels were shown in Table 5.

TABLE 5

Experimental factors and levels for response surface

| Level | A hydrolysis temperature (° C.) | B hydrolysis time (min) | C Sample weight (mg) |
|---|---|---|---|
| −1 | 140 | 10 | 10 |
| 0 | 155 | 25 | 20 |
| 1 | 170 | 40 | 30 |

Step (2): The selenoamino acids in the hydrolysate obtained under the hydrolysis conditions in Table 5 were detected with the HPLC-HG-AFS method under detection conditions as shown in Table 1, Table 2 and Table 3. Detection results of $SeCys_2$, SeMet, SeMeCys and total Se are shown in Table 6.

TABLE 6

Detection results of $SeCys_2$, SeMet, SeMeCys and total Se in the experiment using the designed response surface method

| Sequence number | A Hydrolysis temperature (° C.) | B Hydrolysis time (min) | C Sample weight (mg) | Content of $SeCys_2$ (mg/kg) | Content of SeMeCys (mg/kg) | Content of SeMet (mg/kg) | Content of total Se (mg/kg) |
|---|---|---|---|---|---|---|---|
| 1 | 140 | 10 | 20 | 124.11 | 241.03 | 1951.57 | 2316.71 |
| 2 | 170 | 10 | 20 | 84.28 | 33.68 | 2664.83 | 2782.79 |
| 3 | 140 | 40 | 20 | 158.28 | 122.09 | 2729.48 | 3009.85 |
| 4 | 170 | 40 | 20 | 64.97 | 91.57 | 2291.77 | 2450.40 |
| 5 | 140 | 25 | 10 | 78.44 | 32.30 | 1457.57 | 1568.31 |
| 6 | 170 | 25 | 10 | 37.10 | 113.67 | 1245.87 | 1396.63 |
| 7 | 140 | 25 | 30 | 186.18 | 216.31 | 765.00 | 1200.82 |
| 8 | 170 | 25 | 30 | 56.75 | 189.66 | 1571.58 | 1826.67 |
| 9 | 155 | 10 | 10 | 123.48 | 239.17 | 1196.05 | 1558.70 |
| 10 | 155 | 40 | 10 | 98.09 | 243.60 | 2451.84 | 2795.92 |
| 11 | 155 | 10 | 30 | 52.43 | 51.15 | 1538.61 | 1650.70 |
| 12 | 155 | 40 | 30 | 66.99 | 401.35 | 2239.97 | 2715.34 |
| 13 | 155 | 25 | 20 | 59.29 | 121.43 | 2503.78 | 2684.50 |
| 14 | 155 | 25 | 20 | 66.86 | 285.56 | 2325.95 | 2678.36 |
| 15 | 155 | 25 | 20 | 76.65 | 308.55 | 2178.87 | 2574.91 |
| 16 | 155 | 25 | 20 | 62.82 | 73.58 | 2224.15 | 2360.00 |
| 17 | 155 | 25 | 20 | 60.67 | 124.53 | 2135.92 | 2332.10 |

Figure 2:
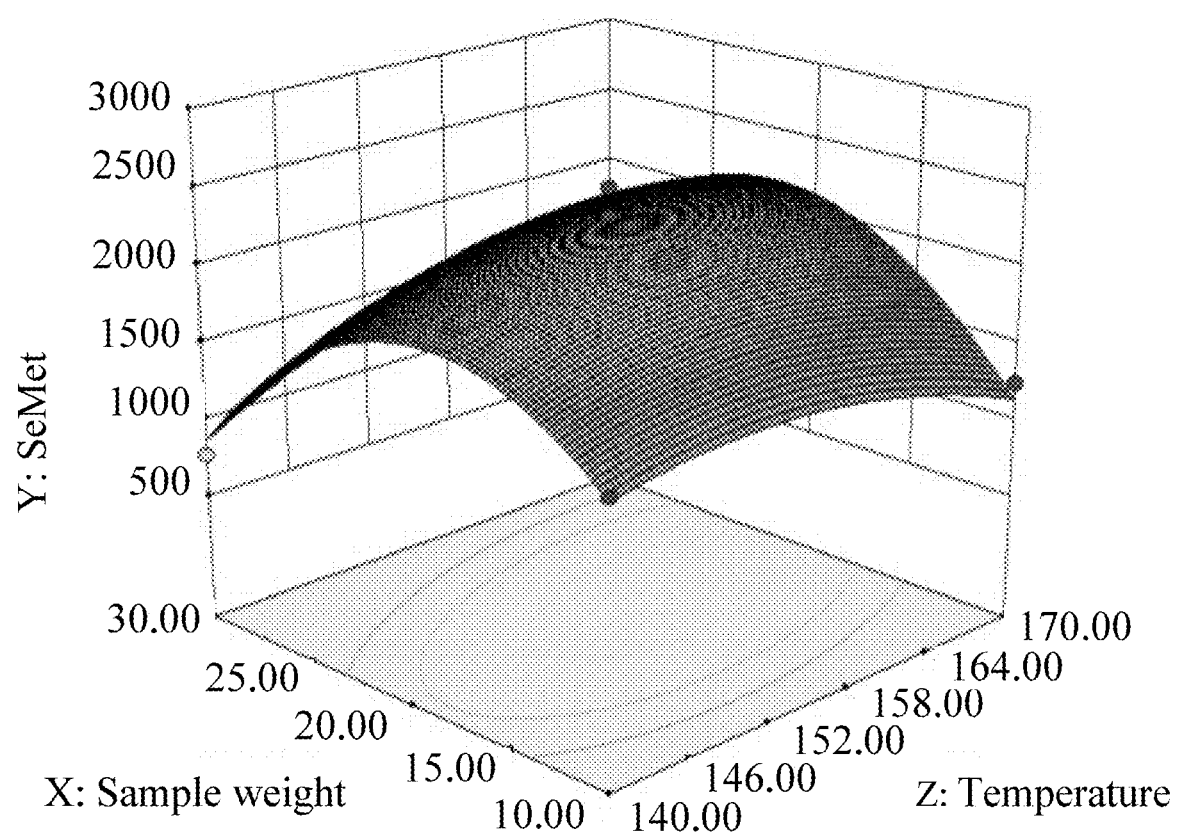
FIG. 2 is a graphical representation of the response surface of Y=f (A, C) in Example 2, where Y is the content of SeMet in the hydrolysate, A is the hydrolysis temperature, and C is the sample weight.
Figure 3:
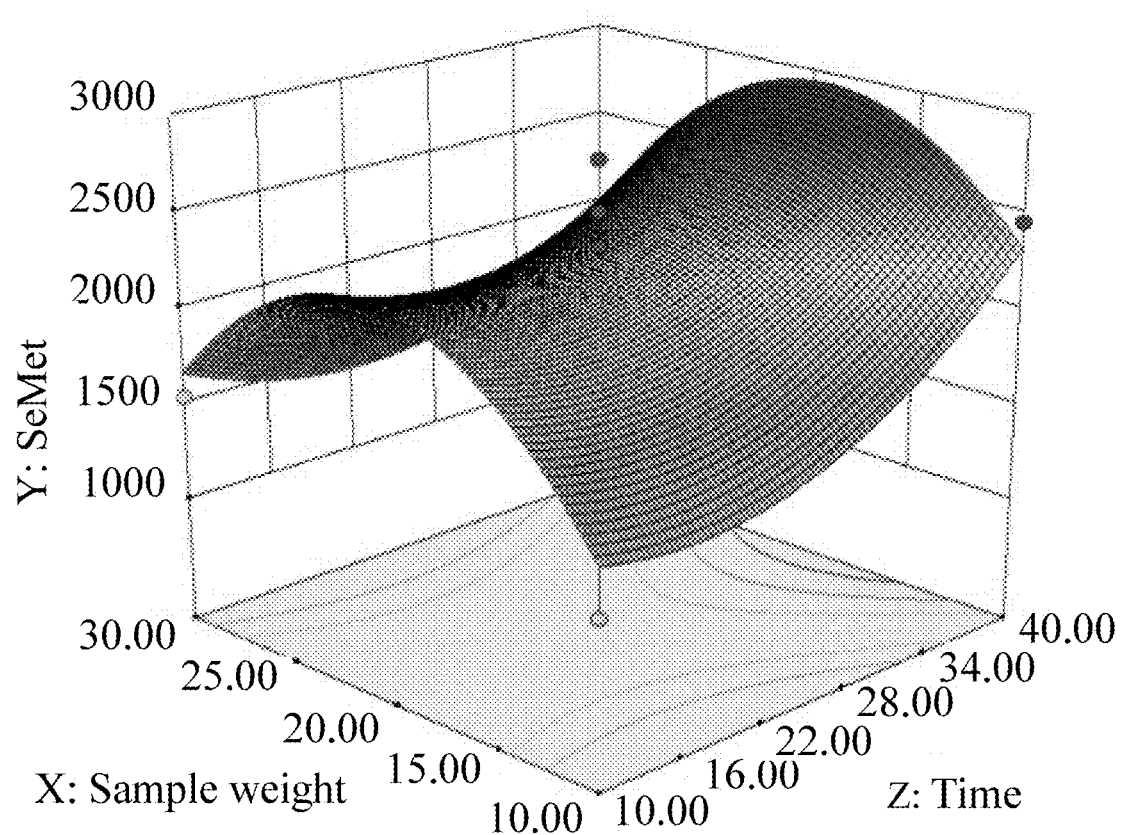
FIG. 3 is a graphical representation of the response surface of Y=f (B, C) in Example 2, where Y is the content of SeMet in the hydrolysate, B is the hydrolysis time, and C is the sample weight.

SeMet was the main product of selenoprotein hydrolysis, so this example used the detection results of the SeMet to determine the interactions between various factors. The interactions between various factors are shown in FIGS. 1, 2 and 3, where FIG. 1 is a graphical representation of the response surface of Y=f (A, B), FIG. 2 is a graphical representation of the response surface of Y=f (A, C) and FIG. 3 is a graphical representation of the response surface of Y=f (B, C). In the figures, A represented the hydrolysis temperature, B represented the hydrolysis time, C represented the sample weight, and Y represented the SeMet content. The interaction between two factors was more significant where the response surface went steeper. It can be seen from FIG. 1 that the optimal hydrolysis temperature was 145-155° C. while the hydrolysis time was 37-40 min. It can be seen from FIG. 2 that the optimal hydrolysis temperature was 155-170° C. while the sample weight was 17.5-25.0 mg. It can be seen from FIG. 3 that the optimal hydrolysis time was 38-40 min while the sample weight was 17.5-22.5 mg.

Step (3): Analysis of variance of the response surface regression model.

Design-expert 8.05b software was used with Box-Behnken Design (BBD) design to perform the response surface analysis based on the data in Table 6. A model was obtained through multiple regression fitting and subjected to analysis of variance. The optimized mathematical regression equation for selenoprotein hydrolysis was obtained as shown in formula I:

$$R=+2273.73+108.80A+295.17B-29.45C-287.74AB+254.57AC-138.46BC-230.39A^2+366.07B^2-783.34C^2 \quad \text{formula I,}$$

Where, R is the content of SeMet (mg/kg) in the hydrolysate, A is the hydrolysis temperature (° C.), B is the hydrolysis time (min), and C is the sample weight (mg) which was also the liquid-to-sample ratio. The F test and analysis of variance were performed on the model with results shown in Table 7.

TABLE 7

Analysis of variance of response surface regression equation

| Source of variance | Sum of squares | Degree of freedom | Mean square | F | P > F | Significant or not |
|---|---|---|---|---|---|---|
| Model | 4.767E+006 | 9 | 5.297E+005 | 8.61 | 0.0048 | Extremely significant |
| A-hydrolysis temperature | 94706.05 | 1 | 94706.05 | 1.54 | 0.2548 | No |
| B-hydrolysis time | 6.970E+005 | 1 | 6.970E+005 | 11.32 | 0.0120 | Significant |
| C-Sample weight | 6936.06 | 1 | 6936.06 | 0.11 | 0.7469 | No |
| AB | 3.312E+005 | 1 | 3.312E+005 | 5.38 | 0.0534 | No |
| AC | 2.592E+005 | 1 | 2.592E+005 | 4.21 | 0.0793 | No |
| BC | 2.584E+006 | 1 | 2.584E+006 | 41.98 | 0.0003 | Extremely significant |
| $A^2$ | 2.235E+005 | 1 | 2.235E+005 | 3.63 | 0.0984 | No |
| $B^2$ | 5.642E+005 | 1 | 5.642E+005 | 9.17 | 0.0192 | Significant |
| $C^2$ | 2.584E+006 | 1 | 2.584E+006 | 41.98 | 0.0003 | Extremely significant |
| Residual | 4.308E+005 | 7 | 61547.53 | | | |
| Lack of fit | 3.447E+005 | 3 | 1.149E+005 | 5.34 | 0.0697 | Not significant |
| Pure error | 86098.12 | 4 | 21524.53 | | | |
| Sum | 5.198E+006 | 16 | | | | |

It can be obtained from the coefficients of the first degree terms of the equation in Table 7 that, factors affecting the content of SeMet were in the following order:

hydrolysis time >hydrolysis temperature >sample weight.

As shown in the results of analysis of variance in the table, the F value of the regression equation was 8.61 while the value under the Prob>F item was less than 0.01, indicating that the model was extremely significant; and B was less than 0.05, showing a significant effect. Through response surface analysis and regression model prediction, the best hydrolysis conditions for a selenoprotein were:

hydrolysis temperature of 149.04° C.;
hydrolysis time of 40.00 min; and
sample weight of 19.24 mg.

The predicted total content of hydrolyzed selenoamino acids (in terms of Se) was 3300.22 mg/kg, which was different from the total Se content in the selenoprotein of 3084.56 mg/kg measured by the national standard method by 6.76%, indicating that the conditions were suitable for the hydrolysis of the selenoprotein. In order to facilitate actual operation, the final hydrolysis conditions were determined as follows:

hydrolysis temperature of 150° C., hydrolysis time of 40 min, and sample weight of 20 mg.

EXAMPLE 3

An accurate amount of 20 mg (accuracy of 0.1 mg) of a Se-rich yeast sample was added into a quartz insert cup. 1.0 mL of 6 mol/L hydrochloric acid solution was added. The insert cup was inserted into a sample holder symmetrically. 150 mL of 6 mol/L hydrochloric acid was added to a 1 L hydrolysis inner tank and put into the sample insert cup holder. The inner tank was put into the outer tank, a cover, a gasket and a spring piece are installed in place and then placed on a holder. Three pressure screws were tightened with a torque spanner and a temperature sensor was inserted. A rotor for protein hydrolysis was placed in the middle of the chamber of the main body of the microwave proteolysis apparatus. A vacuum-pumping flow path of the valve assembly at the top of the apparatus was opened, and closed after evacuation for 2-3 min, and then, a nitrogen flow path was opened to fill in nitrogen (2-3 kg of pressure) for 1-2 min. The operation was repeated 3 times to fill the 1 L inner tank with nitrogen atmosphere to protect the sample. The following procedure was run to increase the temperature: increasing to 150° C. in 15 min, holding for 40 min, and cooling to about 50° C. The rotor for protein hydrolysis and then the insert cup was removed. The sample solution was transferred to a 25 mL small beaker, added with 0.95 mL of 6 mol/L sodium hydroxide. The pH was adjusted to 7.5 with 1 mol/L sodium hydroxide solution on an automatic potentiometric titrator. The solution was transferred to a 25 mL volumetric flask and added with water to the volume. Filtration was carried out with a 0.45 μM syringe filter to collect the filtrate which was then loaded to the HPLC-HG-AFS and detected under conditions shown in Table 1, Table 2 and Table 3. Results showed 115.22 mg/kg of $SeCys_2$, 373.45 mg/kg of SeMeCys, 1260.54 mg/kg of SeMet, and 1755.22 mg/kg of the sum of various forms of Se which was 2.72% in difference with respect to the total Se content of 1803.61 mg/kg measured by the national standard method.

The difference was within an allowable range of measure error. It can be seen from the above examples that, the method for detecting selenoamino acids according to the present invention has simple operation and can quickly and accurately detect the selenoamino acids in selenoproteins.

The above descriptions are merely preferred implementations of the present invention. It should be noted that a person of ordinary skill in the art may further make several improvements and modifications without departing from the principle of the present invention, but such improvements and modifications should be deemed as falling within the protection scope of the present invention.

What is claimed is:

1. A method for detecting a selenoamino acid in a selenoprotein, comprising :
    mixing 10-30 mg of a selenoprotein sample with hydrochloric acid, and hydrolyzing with microwaves at 140-170° C. for 10-40 min to obtain a hydrolysate;
    adjusting a pH of the hydrolysate to 6-8 to obtain a pretreated solution; and
    detecting a selenoamino acid in the pretreated solution using high performance liquid chromatography-hydride generation-atomic fluorescence spectrometry (HPLC-HG-AFS) to obtain a content of the selenoamino acid.

2. The detection method according to claim 1, wherein the selenoprotein sample is in a range of 15-25 mg.

3. The detection method according to claim 2, wherein the selenoprotein sample is 20 mg.

4. The detection method according to claim 1, wherein the hydrolyzing with microwaves is carried out at temperature range of 150-160° C.

5. The detection method according to claim 4, wherein the hydrolyzing with microwaves is performed for 30-40 min.

6. The detection method according to claim 1, wherein the hydrolyzing with microwaves is performed for 30-40 min.

7. The detection method according to claim 1, wherein the pretreated solution has a pH of 7-8.

8. The detection method according to claim 1, wherein the high performance liquid chromatography (HPLC) uses an anion exchange column.

9. The detection method according to claim 1, wherein the content of the selenoamino acid can be detected within 8 min after a test sample is prepared.

* * * * *